United States Patent
Baets et al.

(10) Patent No.: US 10,036,625 B2
(45) Date of Patent: Jul. 31, 2018

(54) INTEGRATED SPECTROMETERS WITH SINGLE PIXEL DETECTOR

(71) Applicants: UNIVERSITEIT GENT, Ghent (BE); IMEC VZW, Leuven (BE)

(72) Inventors: Roeland Baets, Deinze (BE); Danaë Delbeke, Gentbrugge (BE); Günther Roelkens, Schellebelle (BE); Wim Bogaerts, Melle (BE)

(73) Assignees: UNIVERSITEIT GENT, Ghent (BE); IMEC VZW, Leuven (BE)

( * ) Notice: Subject to any disclaimer, the term of this patent is extended or adjusted under 35 U.S.C. 154(b) by 0 days.

(21) Appl. No.: 15/305,713

(22) PCT Filed: Apr. 23, 2015

(86) PCT No.: PCT/EP2015/058764
§ 371 (c)(1),
(2) Date: Oct. 21, 2016

(87) PCT Pub. No.: WO2015/162197
PCT Pub. Date: Oct. 29, 2015

(65) Prior Publication Data
US 2017/0082421 A1     Mar. 23, 2017

(30) Foreign Application Priority Data

Apr. 23, 2014 (EP) .................................... 14165712
Jul. 20, 2014 (EP) .................................... 14177745

(51) Int. Cl.
*G01J 3/28* (2006.01)
*G01B 9/02* (2006.01)
(Continued)

(52) U.S. Cl.
CPC ..... *G01B 9/02051* (2013.01); *G01B 9/02044* (2013.01); *G01J 3/0218* (2013.01);
(Continued)

(58) Field of Classification Search
CPC ........ G01J 3/28; G01J 3/26; G01J 3/02; G01J 3/42; G01J 3/10; G01J 3/43; G01B 9/02; G01N 21/35; G02B 6/12
See application file for complete search history.

(56) References Cited

U.S. PATENT DOCUMENTS

| 4,164,373 A | 8/1979 | Schuss et al. |
| 4,999,489 A | 3/1991 | Huggins |

(Continued)

OTHER PUBLICATIONS

Bockstaele et al., "Glucose Sensing by Means of Silicon Photonics," Proceedings of SPIE, Mar. 8, 2014, pp. 1-8, vol. 8989.
(Continued)

*Primary Examiner* — Abdullahi Nur
(74) *Attorney, Agent, or Firm* — Workman Nydegger

(57) ABSTRACT

An integrated waveguide based spectrometer is described. The spectrometer comprises a sensing region for receiving multi-wavelength radiation for irradiating a sample in the sensing region, a wavelength demultiplexing element arranged for capturing said multi-wavelength radiation after interaction with the sample and for providing a number of wavelength demultiplexed radiation outputs or a number of different groups of wavelength demultiplexed radiation outputs, an integrated modulator for differently modulating the different demultiplexed radiation outputs or different groups of demultiplexed radiation outputs, and a multiplexer element for multiplexing the differently modulated demultiplexed radiation outputs or the differently grouped demultiplexed radiation outputs.

20 Claims, 4 Drawing Sheets

(51) Int. Cl.
  *G01J 3/02* (2006.01)
  *G01J 3/18* (2006.01)
  *G01J 3/32* (2006.01)
  *G01J 3/433* (2006.01)
  *G01N 21/35* (2014.01)
  *G02B 6/12* (2006.01)

(52) U.S. Cl.
  CPC ........... *G01J 3/0256* (2013.01); *G01J 3/0259* (2013.01); *G01J 3/18* (2013.01); *G01J 3/1895* (2013.01); *G01J 3/32* (2013.01); *G01J 3/433* (2013.01); *G01N 21/35* (2013.01); *G02B 6/12019* (2013.01)

(56) References Cited

U.S. PATENT DOCUMENTS

| | | |
|---|---|---|
| 2002/0057431 A1 | 5/2002 | Fateley et al. |
| 2005/0036667 A1* | 2/2005 | So .................... G06K 9/00127 382/128 |
| 2007/0146700 A1* | 6/2007 | Kowarz .................... G01J 3/02 356/310 |
| 2007/0285658 A1 | 12/2007 | Claps et al. |
| 2008/0087078 A1* | 4/2008 | Vannuffelen .......... E21B 47/102 73/152.54 |
| 2011/0090499 A1* | 4/2011 | Van Der Mark .... A61B 5/0059 356/327 |
| 2013/0321816 A1 | 12/2013 | Dattner et al. |

OTHER PUBLICATIONS

Extended European Search Report for corresponding European Application No. 14177745.8, dated Oct. 24, 2014.
International Search Report for corresponding International PCT Application No. PCT/EP2015/058764, dated Feb. 8, 2016.
Soref, "Towards Silicon-Based Longwave Integrated Optoelectronics (LIO)," Proceedings of SPIE, dated Feb. 6, 2008, pp. 1-13, vol. 6898.

\* cited by examiner

INTEGRATED SPECTROMETERS WITH SINGLE PIXEL DETECTOR

FIELD OF THE INVENTION

The invention relates to the field of sensors. More specifically it relates to methods and systems for performing a method of spectrometry using integrated photonics circuits, such as for example infrared analysis and an infrared spectrometer using integrated photonics circuit.

BACKGROUND OF THE INVENTION

The number of applications of spectrometry is constantly growing, reaching a wide range of applications like security, automotive applications, public healthcare, medical analysis and diagnosis, etc. Especially in personal healthcare, medical analysis and diagnosis, this creates a need for miniaturization and portability of spectrometers.

In the present, spectrometry is one of the easiest and least invasive techniques of analysis. A wide range of analysis is available, for instance spectroscopy based on absorption, emission, secondary emission, elastic and inelastic scattering, refraction spectroscopy, etc. Some integrated sensors based on optical characterization that can be implanted in the body of a living being have been disclosed in the past.

In order to obtain appropriate miniaturization, integrated spectrometers, that analyze the spectrum of a broadband source can be implemented on a photonic integrated circuit. Large channel count spectrometers can be realized. However, in order to obtain a fully integrated spectrometer, large detector arrays integrated with the spectrometers are required. While this is typically not an issue for applications in the visible/near-infrared, it is more cumbersome in the short-wave and mid-infrared (>1.6 um), due to the lower yield of highly sensitive, preferrably not actively cooled photodetectors in this wavelength range. It is however this wavelength range that is often of high importance for spectroscopic sensing applications. The short-wave and mid-infrared region can for example advantageously be used for spectroscopic detection of glucose or urea levels and gas compounds such as $CO_2$, $CO$, $NO$.

In order to guarantee good performance, especially in the infrared radiation range, one typically needs to cool the detector arrays used. Cooling systems, aside of increasing the complexity and size of the device, typically consume a great amount of power. This power consumption has to be added to the power used for the transistors and components of the sensing arrays.

SUMMARY OF THE INVENTION

It is an object of embodiments of the present invention to provide good and reliable integrated spectrometer systems for sensing substances or properties as well as corresponding monitoring systems. Sensing substances may include detecting or identifying targets of interest, but also may include sensing a sample for imaging it.

It is an advantage of embodiments of the present invention that an integrated spectrometer system, e.g. an implantable integrated spectrometer sensor or a spectrometer sensor for mobile devices, is provided that has a good, i.e. not too high, power consumption.

It is an advantage of embodiments of the present invention that an integrated spectrometer system, e.g. an implantable integrated spectrometer sensor or a spectrometer sensor for mobile devices, is provided that is reliable without requiring too much expensive components, thus rendering the integrated spectrometer available for widely spread use.

It is an advantage of embodiments of the present invention that advantages indicated in the present description can be obtained while having a high yield of detection, resulting in accurate measurements.

It is an advantage of embodiments of the present invention that integrated spectrometer systems are provided with a good energy and/or cooling behavior. It is an advantage according to embodiments of the present invention that a detector with only one or a limited number of pixels needs to be cooled and not a large detector array. According to some embodiments, the detector can be a single pixel detector.

It is an advantage of embodiments of the present invention that use can be made of broadband radiation sources, which can be integrated in the systems.

It is an advantage of embodiments of the present invention that, although no large detector array is used, a multi-wavelength, e.g. relative broad wavelength range, radiation can be used, allowing accurate detection of substances, such as for example glucose or urea by analysis of spectral contributions at different spectral wavelengths or wavelength ranges.

It is an advantage of embodiments of the present invention that systems and methods can be provided that are less susceptible for noise, i.e. the sensor output can for example be selected to lie in a range where the 1/f noise is negligible.

It is an advantage of embodiments according to the present invention that an integrated spectrometer is obtained that can be implemented as implantable single-chip optical sensor for continuous monitoring, e.g. continuous glucose monitoring (CGM). It is an advantage of embodiments according to the present invention that the integrated spectrometer sensor can be made small, resulting in good implantation properties.

The above objective and/or one or more of the advantages may be accomplished by systems and/or methods according to one or more embodiments of the present invention.

According to one aspect, some embodiments of the present invention relate to an integrated waveguide based spectrometer comprising a sensing region for receiving multi-wavelength radiation interacting with a sample in the sensing region, a wavelength demultiplexing element arranged for capturing said multi-wavelength radiation after interaction with the sample and for providing a number of wavelength demultiplexed radiation outputs or a number of different groups of wavelength demultiplexed radiation outputs, an integrated modulator for differently modulating the different demultiplexed radiation outputs or different groups of demultiplexed radiation outputs, and a multiplexer element for multiplexing the differently modulated demultiplexed radiation outputs or the differently grouped demultiplexed radiation outputs. It is an advantage of embodiments of the present invention that no large detector arrays are required, while still obtaining accurate spectral results. It is an advantage of embodiments according to the present invention that a configuration is used allowing good integration of the spectrometer, thus resulting in the possibility to obtain a fully integrated spectrometer, using a single pixel or limited pixel detector. It furthermore is an advantage that a better power and/or cooling behavior can be obtained for the integrated spectrometer. It is an advantage that the spectrometer can be made compact and does not require expensive detector arrays.

The wavelength demultiplexing element and the integrated modulator may be an in-plane wavelength demultiplexing element and an in-plane integrated modulator. It is an advantage of embodiments according to the present invention that a configuration is used allowing good integration of the spectrometer, thus resulting in the possibility to obtain a compact integrated spectrometer.

The integrated modulator may be adapted for modulating an intensity or frequency without redirecting the radiation. The fact that the modulation can be performed in a radiation beam without the need for redirecting the radiation beam may result in a compact configuration, thus allowing a compact integrated spectrometer.

In embodiments of the present invention, the multiplexer thus may be a grating array and/or other output coupling element below the detector or butt-coupled to the detector or the multiplexer may be distanced from the detector and guiding means are provided for directing the multiplexed signal to the detector.

The integrated spectrometer may be based on planar lightwave circuits, which are considered encompassed by waveguide based spectrometers.

The integrated spectrometer may comprise the detector, the detector being a single-pixel detector, whereby the multiplexer element may be configured for multiplexing the outputs towards the detector. The multiplexer element may alternatively comprise a detection functionality for detecting the radiation in the integrated spectrometer as a single pixel detector.

The integrated spectrometer may comprise the detector, the detector being a balanced single-pixel detector pair, whereby the multiplexer element may be configured for multiplexing the outputs towards the balanced detector pair, whereby the signal and the reference are guided towards respective detectors in the detector pair. The multiplexer element may alternatively comprise a detection functionality for detecting the radiation in the integrated spectrometer as a balanced detector pair.

In some embodiments, the integrated spectrometer may comprise a large number of channels, whereby the modulated signals are again multiplexed and sent to a single detector or wherein the integrated spectrometer comprises a number of detectors, but the number of detectors is smaller than the number of modulated channels.

The detector may be a thermopile. The detector may be a photon detector or a thermal detector. The detector may be a photovoltage or photocurrent output detector.

The integrated spectrometer further may comprise a radiation source for providing the multi-wavelength radiation.

The modulator may be adapted for time sequential differently modulating the different demultiplexed radiation output or different groups of demultiplexed radiation outputs.

The radiation source may be a broadband radiation source.

The modulator may be an intensity modulator adapted for modulating the different demultiplexed radiation outputs or the different groups of radiation outputs at different frequencies.

The modulator may be adapted for generating orthogonal analog signals of all output channels. The modulator may be adapted for inducing a sinusoidal modulation of all output channels.

The modulator may be arranged for inducing orthogonal digital coding of the output signals of the different demultiplexed radiation outputs or the different groups of demultiplexed radiation outputs.

The modulator may be arranged for modulating the different demultiplexed radiation outputs or the different groups of demultiplexed radiation outputs, by subsequently shutting all outputs of the demultiplexing element except for one or a group of demultiplexed radiation outputs.

The modulator furthermore may be adapted for modulating the signals at a frequency outside the 1/f noise of the detector.

The modulator may be a thermal modulator arranged for inducing thermal modulation of a balanced Mach-Zehnder interferometer.

The modulator may be an electro-optic modulator arranged for inducing electro-optic modulation of a balanced Mach-Zehnder interferometer.

The modulator may be an electro-absorption modulator.

The electro-absorption modulator may be a graphene based electro-absorption modulator. It is an advantage of embodiments of the present invention that very broadband electro-absorption modulators can be used.

The spectrometer furthermore may comprise a demodulator for demodulating the signal detected in the detector.

The demodulator may be a hardware-based demodulator.

The demodulator may comprise a lock-in amplifier for lock-in amplification at the various modulation frequencies induced by the modulator.

The demodulator may be a software based demodulator.

The demodulator may be an FPGA based demodulator.

The demodulator may be implemented in digital software.

The demodulator may be programmed for demodulating the signal after analog to digital conversion.

The demodulator may be programmed for performing Fast Fourier Transform.

The demultiplexing element may comprise any of a photonic crystal, tunable filters, an echelle grating, an arrayed waveguide grating, a planar concave grating, a ring resonator based spectrometer, a Mach-Zehnder Fourier transform spectrometer (e.g. a Mach-Zehnder based Lattice filter), a diffractive grating or a grating embedded in a waveguide, or a Mach-Zehnder Fourier transform spectrometer, or any other system suitable for the radiation used or any combination thereof. The output of the demultiplexing element is a plurality of signals, each of which may be characterized by a specific wavelength, or a frequency, or a narrow band of frequencies.

The demultiplexing element may be an in plane demultiplexing element.

The modulator may be an in plane modulator and may comprise for example micro-ring modulators, electo-absorption modulators, mach-zechnder modulators, etc.

The modulator may be positioned downstream the demultiplexing element with respect to the radiation source providing the multi-wavelength radiation.

Multiplexing the outputs may comprise intensity modulating the output of different output channels or different groups of output channels unique for each of the different output channels or unique for the different groups of output channels.

The spectrometer may comprise a reference region, a wavelength demultiplexing element, a modulator and a multiplexer element, for generating corresponding modulated demultiplexed output signals and multiplexing them.

The modulated demultiplexed reference output signals or grouped modulated demultiplexed reference output signals may be directed to a same detector as the differently modulated demultiplexed radiation outputs or the differently grouped demultiplexed radiation outputs stemming from the sensing region. The integrated spectrometer may be particularly configured therefore.

The spectrometer may comprise a beam splitter for splitting the multi-wavelength radiation to the sensing region and a reference region. It is an advantage of embodiments of the present invention that both lines have substantially the same spectrum.

The detector may comprise a readable photocurrent output. The detector may be a thermopile. The detector may be a photon detector or the detector may be a thermal detector. The detector may comprise a readable photovoltage or photocurrent output. It is an advantage of embodiments of the present invention that the output signal can be read as power spectral density.

The spectrometer may comprise one or more optical waveguides. It is an advantage of embodiments of the present invention that the sensor can be made highly versatile.

The integrated spectrometer may be integrated in a photonics integrated circuit. It is an advantage of embodiments of the present invention that the sensor can be integrated in a system-on-chip or a system-on-package.

The integrated spectrometer may be embedded in an implantable sensor system.

According to one aspect, embodiments of the present invention relate to a method for characterizing a sample property using spectrometry, the method comprising, allowing multi-wavelength radiation to interact with a sample to be characterized, demultiplexing the multi-wavelength radiation into different signal carriers after interaction of the multi-wavelength radiation and the sample to be characterized, modulating in an integrated modulator different demultiplexed radiation outputs or different groups of demultiplexed radiation outputs in a different way in the different signal carriers, and multiplexing the differently modulated demultiplexed radiation outputs or the differently grouped demultiplexed radiation outputs towards a detector.

Said modulating may comprise modulating an intensity and/or frequency of the radiation without redirecting (i.e. inducing a different propagation direction for) the radiation in the modulator.

The method may furthermore comprise splitting multi-wavelength radiation into radiation to be passed through a sensing region, the sensing region being the region where the sample to be characterized is to be positioned, and reference radiation to be passed through a reference region.

The method may furthermore comprise demultiplexing the multi-wavelength reference radiation passing through the reference region, modulating the different demultiplexed reference radiation outputs or groups of demultiplexed reference radiation outputs in a different way, and multiplexing the differently modulated demultiplexed reference radiation outputs or the differently grouped demultiplexed reference radiation outputs.

The reference radiation and the radiation passing through the sensing region may be modulated differently for unequivocally labeling the radiation outputs.

The method may comprise comparing each output signal component of multi-wavelength radiation that has interacted with a sample to be characterized with a corresponding reference output signal component of a reference beam of multi-wavelength radiation.

According to one aspect, embodiments of the present invention relate to the use of an integrated spectrometer for characterizing or detecting a component of the sample. The Sample may be a substance, such as a gas, a liquid, a mixture thereof, etc.

According to one aspect, embodiments of the present invention relate to the use of an integrated spectrometer in an implantable sensor for characterizing a property of a substance in an object.

According to one aspect, embodiments of the present invention relate to the use of an integrated spectrometer in an implantable sensor for characterizing a property of a substance in a living creature. The use may be for characterizing a glucose or urea level in a living creature.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
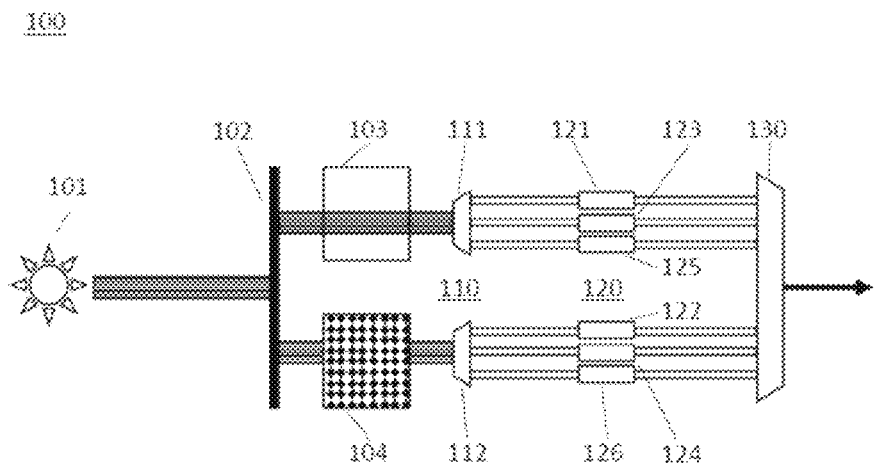
FIG. 1 schematically shows a schematic representation of an exemplary sensor for analysis according to embodiments of the present invention.

The drawings are only schematic and are non-limiting. In the drawings, the size of some of the elements may be exaggerated and not drawn on scale for illustrative purposes. Any reference signs in the claims shall not be construed as limiting the scope.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, specific details are set forth. However, it is understood that embodiments of the invention may be practiced without these specific details. In other instances, well-known methods, structures and techniques have not been shown in detail in order not to obscure an understanding of this description.

In embodiments of the present invention regard "radiation" as "electromagnetic radiation", for instance radiation within the range between far infrared to ultraviolet.

In a first aspect, embodiments of the present invention may relate to an integrated waveguide based spectrometer. Such an integrated spectrometer may be implemented as a photonics integrated circuit. The spectrometer comprises a sensing region for receiving multi-wavelength radiation for irradiating a sample in the sensing region. The sensing region may be coated with a chemical or bio-chemical layer so that for example concentration enhancement for the target analyte can be obtained. The spectrometer also comprises a wavelength demultiplexing element arranged for capturing said multi-wavelength radiation after interaction with the sample and for providing a number of wavelength demultiplexed radiation outputs or a number of different groups of wavelength demultiplexed radiation outputs. The spectrometer furthermore comprises a modulator for differently modulating the different demultiplexed radiation outputs or different groups of demultiplexed radiation outputs and a multiplexer element for multiplexing the differently modulated demultiplexed radiation outputs or the differently grouped demultiplexed radiation outputs. The output may be multiplexed to a detector or the multiplexer may have a detection functionality.

In advantageous embodiments, the spectrometer may comprise a reference channel for generating reference output signals, whereby the reference output signals may be demultiplexed, modulated and multiplexed and whereby the reference output signals may be detected using the same detector as the sensing signals. The reference output signals and the sensing signals may be modulated differently or may be modulated in the same way. The reference output signals and the sensing signals are combined in the detection unit, e.g. to compensate for variations in the radiation source, the detector, etc.

The spectrometer may be based on planar Lightwave circuits, which are considered encompassed in waveguide based spectrometer.

By way of illustration, optional features and advantages according to at least some embodiments of the present invention will be described below, embodiments of the present invention not being limited thereto.

In one embodiment a spectrometer system is provided wherein a conventionally used large detector array is replaced by a single pixel detector. The detector may be a photon detector or a thermal detector. The detector may be a thermopile. The latter advantageously impacts the spectrometer cost. Embodiments of the present invention also may impact power consumption, since only a single pixel detector is to be cooled instead of a large array.

It is an advantage of embodiments of the present invention that spectroscopic sensing applications can benefit from spectrometers that are cheap, small and good performance resolution. Embodiments of the present invention include spectroscopy of liquids and low resolution spectroscopy of gases.

Embodiments of the present invention may be advantageously used for silicon photonics spectrometers for the continuous measuring of substances such as for example glucose or urea concentrations using a body implant.

Embodiments of the present invention may advantageously be used for gas sensing e.g. for air quality monitoring, security, safety. In some embodiments sensing in food packages may be used for detecting early spoilage.

According to at least some embodiments of the present invention, the spectrometer may comprise a radiation carrier for carrying multi-wavelength radiation from a source. Such radiation carriers may be waveguides. The spectrometer may comprise a sensing channel and a reference channel. In the sensing channel the multi-wavelength radiation generated by an external or internal radiation source interacts with a substance to be analyzed. The substance may be any suitable substance, such as for example a pellet, or a solution (fluid), or a gas The region where the interaction between the multi-wavelength and the substance may be referred to as the sensing region or detection region. The interaction of the substance with the radiation affects the latter, changing at least one of its characteristics with respect to the reference radiation. According to at least some embodiments, the effect may be a change in an spectral component of the multi-wavelength radiation. The radiation may be guided, after interaction with the sample, to a demultiplexer element. The demultiplexing element is suitable for separating different spectral contributions.

As an output of the demultiplexing element, in particular embodiments of the present invention, a number of signal outputs (signal lines) may be present in the sensing channel and the same number of signal outputs (signal lines) may be present in the reference channel, and the outputs of the reference may correspond reciprocally with the outputs of the sensing channel. The output signals can be modulated in the same manner, e.g. with a unique frequency, so each signal is unequivocally labelled for further comparison.

After modulation of the output signals so that the different spectral contributions are uniquely identifiable, the signals are fed to a detector with a limited number of pixels, e.g. a single pixel photodetector. According to embodiments of the present invention, the number of pixels of the detector is smaller than the number of spectral contributions one wishes to identify. The output of the detector may give information regarding the composition of the sample. This operation may be performed, in certain embodiments of the present invention, by comparison of each signal from the sampling line with each signal of the reference line. For instance, in case of absorption infrared spectroscopy, different absorption spectral contributions can be obtained and compared with the reference. In each case, cross talk or mixed signals can be advantageously reduced or avoided, because each of them may be labelled by a different modulation. The need for a detector array is advantageously avoided, hence simplifying the circuitry and improving functionality. Additionally, if cooling is required, which typically is the case for increasing the yield, a cooling system may be present but the cooling system may advantageously reduced and simplified with respect to conventional spectrometers, as the possible cooling needs may be reduced to cooling a single detector instead of a detector array.

Embodiments or parts of embodiments of the first aspect of the present invention, the present invention not being limited thereto, are schematically shown in FIG. 1 to FIG. 4.

As a particular, non-limiting embodiment of the present invention, FIG. 1 schematically shows an integrated spectrometer 100 suitable for analyzing a material, for example but not limited to a gas, or a liquid, or a material in solution, the present invention not being limited by any specific type of sample. The radiation source 101, which may be integrated in the sensor or may be external, may be a multi-spectral source, like a broadband source, a Light Emitting Diode (LED), an incandescent bulb, a halogen bulb, or based on laser technology, the present invention not being limited to any specific type of source. Certain embodiments of the present invention may comprise a divider 102, for division of the incident radiation in two channels, e.g. a sensing channel and a reference channel. The divider 102 may comprise a beam splitter, a fiber optic splitter, a system comprising mirrors, semi-reflective coated surfaces, the present invention not being limited thereto. The channels themselves may comprise radiation carriers like optical fiber, optical nanofiber, PLC e.g. polymer or glass/silica waveguides, Al—Ga—As waveguides, In(Ga)(As)P waveguides, high-index contrast waveguides such as silicon on insulator (SOI), photonic crystal fiber, striplines, any other suitable carrier or any combination thereof. The system thus may comprise two channels, the sensing channel and the reference channel, may carry substantially the same information from the source to the measurement regions. Certain embodiments of the present invention comprise only a sensing channel. Certain embodiments of the present invention may comprise a divider 102 that divides the incident radiation in two or more lines, for example for reference and for sensing.

The particular embodiment schematically shown in FIG. 1 comprises two channels, a reference and a sensing channel. In the schematic, all elements comprised in the reference channel have odd numbers, while all elements comprised in the sampling channel are indexed by even numbers, while certain numbers 110, 120, 130 correspond to demultiplexer and multiplexer elements.

The reference channel may carry multispectral information through a region 103 containing a reference, for example a known reference material or corresponding with a blank, e.g. using a vacuum or covering layer, e.g. oxide or polymer. The sensing channel may carry multispectral information through a sensing region 104 containing a substance of interest. The sensing region may comprise a cannula, a probe, a vial, a pellet, or in any suitable sample holder. The system may be covered with a suitable covering material while leaving open the sensor area. The geometry of both lines can be tailored so the characteristics of the radiation in both lines differ mainly in the spectral contribution of the substance. For instance, the optical path length of the radiation may be substantially equal in both lines.

The radiation in the lines can then be guided to a demultiplexing element 111 for the reference channel and a demultiplexing element 112 for the sampling channel. Both demultiplexing elements 111 and 112 may be advantageously substantially identical, so they provide the same number of signals, and there is a correspondence between each signal of the reference line with each signal of the sampling line. The demultiplexing element may comprise spectrometer elements, for example comprising a photonic crystal, tunable filters, an echelle grating, an arrayed waveguide grating, a planar concave grating, a ring resonator based spectrometer, a Mach-Zehnder Fourier transform spectrometer (e.g. a Mach-Zehnder based Lattice filter), a diffractive grating or a grating embedded in a waveguide, or a Mach-Zehnder Fourier transform spectrometer, or any other system suitable for the radiation used or any combination thereof. The output of the demultiplexing element is a plurality of signals, each of which may be characterized by a specific wavelength, or a frequency, or a narrow band of frequencies. The sensor may further comprise a multiplexer system 120. The multiplexing of the signals may comprise modulating each signal by the introduction of a system for manipulating and labelling each signal, for example but not limited to a set of modulators 121, 122, 123, 124, 125, 126, and a detector 130. The multiplexing may be done by intensity modulation of each signal according to a signal-specific modulation (unique for each signal or group of signals in the channel), so the output of the detector 130 can provide all contributions of each signal in a distinguishable way. The spectrometer according to embodiments of the present invention may comprise signal carriers from the demultiplexing element 110 to the multiplexer system 120. Hence, each signal extracted in the demultiplexing element system 110 may be the input of the multiplexer system, for instance the input of the modulators 121, 122, 123, 124, 125, 126. The multiplexer system may comprise any kind of multiplexing system, for instance code division multiple access, frequency division or time domain multiplexing, or other types or combination of types, the present invention not being limited thereto. The signals in the reference line may be modulated in the modulators 121, 123, 125, each of which modulates each signal with a different modulation such as for example a different modulation frequency.

Each of the signals in the sensing channel thus may be modulated by modulators 122, 124, 126, each signal being modulated with a different frequency. As each signal in the sensing channel corresponds reciprocally with each signal in the reference channel, each signal of the sensing channel may be modulated with the same frequency as its reciprocal signal in the reference channel, so each pair of modulators 121 and 122, 123 and 124, 125 and 126 of corresponding signals may produce the same modulation. Embodiments of the present invention may not be limited thereto, for instance each signal in the sensing channel may be modulated by a multiple of the modulation frequency of its corresponding signal in the reference channel, or for instance each signal in both lines may be differently modulated Different modulation schemes can be used, for instance sinusoidal modulation of all channels at different frequencies, or orthogonal digital coding, or by methods based on time-division multiplexing, the present invention not being limited to any particular modulation technique. Moreover, different principles may be used for modulation. For example, thermal modulation of a balanced Mach-Zehnder (MZ) interferometer adapted for optical broadband may be advantageously simple to implement. Electro-optic modulation of a balanced MZ interferometer or electro-absorption broadband modulators can also be used. Moreover, any combination or addition of such techniques may also be used. Particular embodiments of the present invention, the present invention not being limited thereto, may include time-division multiplexing further comprising modulation, for instance by shutting off all the signal channels of the spectrometer except for one signal, which may be further modulated by a different technique, advantageously reducing the 1/f noise in the detector.

Due to the modulation, each signal in the sensing channel can then be labelled and can be compared with its corresponding reference signal. The output of the detector may unravel the individual contributions of each wavelength signal or wavelength range signal, and the sensor according to embodiments of the present invention can advantageously use only one detector 130. The detector may be implemented in CMOS technology and/or comprise a membrane, a thermopile, or any other suitable technology. It may further comprise a cooling system, which may be advantageously simple with low power consumption compared to cooling of a detector array.

Figure 2:
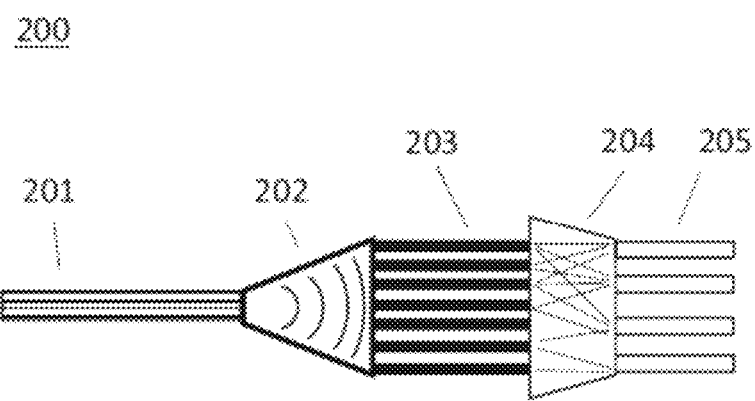
FIG. 2 schematically shows an example of a part of a demultiplexing element, as can be used in embodiments of the present invention.

FIG. 2 shows schematically a demultiplexing element system 200 according to some embodiments of the present invention, the present invention not being limited to this example. The system may comprise a radiation carrier 201, for example a waveguide for carrying radiation as output of a reference region, or as output of a sample region. The waveguide is connectable to an arrayed waveguide grating (AWG) comprising an input 202, like a free propagation region or any other suitable input, optical guides 203 like a decoupled waveguide array, and an output 204 like a free propagation region comprising output signal carriers 205, for instance optical guides. Each of such signal carriers may deliver the signal to a modulator system according to embodiments of the present invention, for instance to a thermo-optical or electro-optical modulation system, before introducing the signals in the detector. Specific properties of the array, like the free spectral range, geometry, etc. should be chosen according to each particular application and radiation range. The system may be part of an integrated circuit.

Figure 3:
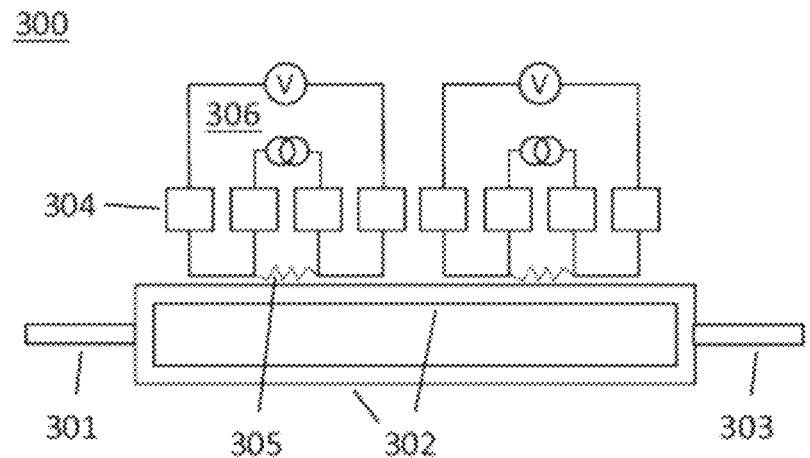
FIG. 3 schematically shows an example of a modulator based on thermo-optics, as can be used in embodiments of the present invention.

As an example of embodiments of a modulation system suitable for the present invention, the present invention not being limited thereto, a thermo-optical modulator 300 is schematically shown in FIG. 3, comprising a single signal channel comprising an input 301, optical waveguides 302 and an output 303, further comprising electrical pads 304 and resistive heaters 305. The electrical pads may be connectable to a power source and voltage regulator 306. The modulation is obtained by heating the waveguide, changing its refraction index. For instance, modulation can be performed by changing the temperature of the waveguides and shutting off all signal channels, thereafter concomitantly letting the radiation pass through the waveguide one channel at a time, at a given frequency M, effectively creating a time-division modulation with a modulation frequency M. Although in the FIG. 3 two heaters are shown, each modulator may comprise only one heater, or more than two, for example five. The power consumed by the thermal modulation may be provided by power sources, and the thermal design of the system can be optimized to keep power consumption to a minimum. Alternatively or additionally to this type of modulation, other non-limiting embodiments of the present invention may comprise electro-optical modulation, for example comprising coplanar waveguides, or electro-absorption modulation using broadband modulators (for example broadband modulators comprising graphene). The modulation system can be comprised in the integrated circuit, analogously to the demultiplexing system in FIG. 2.

The output of the modulation system may be introduced in a detector, for example a single pixel photodetector, like a detector based in CMOS technology, or any other suitable detector. The detector may then act as a multiplexer, resulting in one output signal comprising all the relevant information of the signals entering the detector. All modulated waveguides may be coupled to a single detector using e.g. a grating coupler (e.g. a (5 to 10 µm×5 to 10 µm grating). The latter can for example advantageously be used when hybrid integration is used. Alternatively, a number of channels is multiplexed and the multiplexed signal(s) are sent to the detector. The latter may for example be advantageous in case of an integrated detector such as a photodetector or a thermopile. The signal generated by the detector may be demodulated in any suitable way, e.g. by lock-in amplification of the plurality of the modulation frequencies, according to embodiments of the present invention. Nonetheless, other methods may be used, for instance analog to digital conversion (ADC) and a suitable technique, like a technique based on Fast Fourier Transform (FFT). A Field-Programmable Gate Array (FPGA) or a microprocessor may be comprised for demodulation of the output signal, according to certain embodiments of the present invention. The output may be connectable to a readable device or to an information transmitter.

Figure 4:
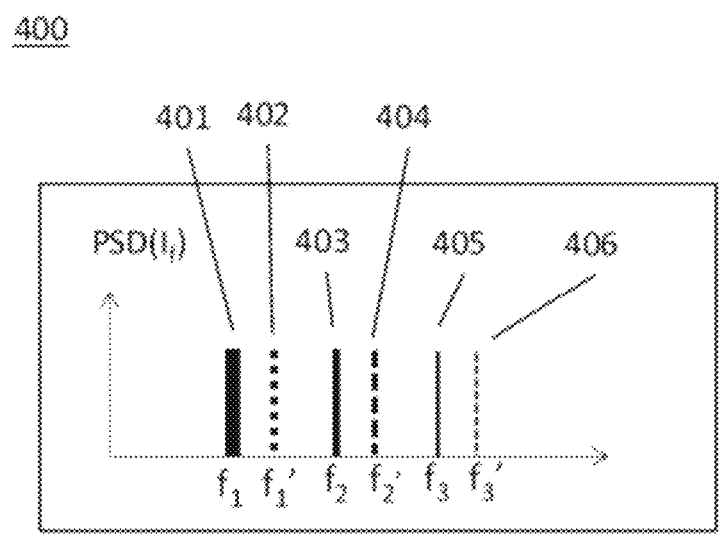
FIG. 4 shows a possible output of a sensor according to an embodiment of the present invention.

For instance, FIG. 4 shows an example of output signal 400 according to certain embodiments of the present invention. In this particular embodiment, the present invention not limited thereto, the spectrometer may be based on absorption spectroscopy. The demultiplexing of three different wavelength channels in the photocurrent is done by amplitude modulation of each output of the spectrometer using a unique frequency for each signal, which can be detected in the photocurrent as different peaks at different labelling frequencies determined by the modulator. The output can be the power density spectrum PSD show in the FIG. 4. The pairs of signals provided by modulators 121 and 122, 123 and 124, 125 and 126 of FIG. 1 can correspond to the pairs of signals 401 and 402, 403 and 404, and 405 and 406, in which the signals with odd reference numbers 401, 403 and 405 correspond to signals of the reference line (carrying information of the reference region) and the signals with the even reference numbers 402, 404 and 406 correspond to their corresponding signals of the sampling line, carrying information of the sampling region. Because each signal is modulated with a fixed, known frequency ($f_1 \ldots f_3$ for the reference signals, $f'_1 \ldots f'_3$ for the sampling signals), each signal can be unequivocally read, so the comparison between the sampled signal and the reference signal is advantageously enabled using a single photodiode. Other suitable outputs and modulation frameworks are also possible.

A sensor according to embodiments of the first aspect of the present invention may be a portable sensor, for instance further comprising a connection to a power source. The sensor according to embodiments of the present invention may be suitable for medical monitoring applications, for analysis of glucose, for example glucose in solution, or for urea. It also may be used for chemical analysis of gases, for instance in automotive applications or in industry, or also in food packaging, for instance for detection of contamination. According to embodiments of the present invention, some of the parts or the whole sensor may be part of a photonics integrated circuit, for example a System-On-Chip or System-On-Package.

As a second aspect of embodiments of the present invention, the present invention not being limited thereto, a method of analysis is presented. The method for characterizing a sample property using spectrometry may comprise allowing multi-wavelength radiation to interact with a sample to be characterized, demultiplexing the multi-wavelength radiation after interaction of the multi-wavelength radiation and the sample to be characterized, modulating different demultiplexed radiation outputs or different groups of demultiplexed radiation outputs in a different way, and multiplexing the differently modulated demultiplexed radiation outputs or the differently grouped demultiplexed radiation outputs towards a detector.

Figure 5:
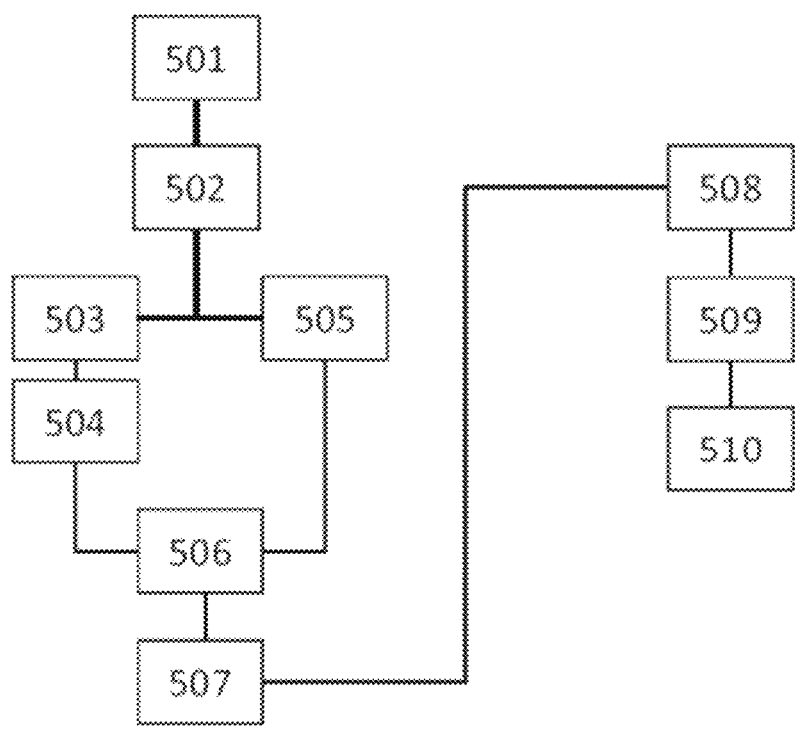
FIG. 5 shows a flowchart according to an exemplary method according to an embodiment of the present invention.

Embodiments of the present method may comprise the steps shown as a flowchart 500 in FIG. 5, the present invention not being limited by these steps. In a first step, a radiation is provided 501. The radiation may be for example visible light, infrared, monochromatic, broadband, the present invention not being limited thereto. A plurality of channels may be used, e.g. a sensing channel and a reference channel or multiple sensing channels. The multi-wavelength radiation may be spread over the different channels by dividing 502 the radiation from a single source, although other methods are also possible. Dividing 502 the radiation, if needed, may be performed by a beam splitter, a fiber optic splitter, or any other suitable technique. Dividing 502 the radiation may also comprise dividing the radiation in two channels, a reference channel and a sampling channel, wherein both lines carry substantially identical information before entering 503 the measurement regions. Entering the measurement region may comprise radiation interacting 504 with a sample. Interaction may comprise absorption, inelastic scattering, or other type of interaction known in the field of spectroscopy or influencing the radiation in any other way. In certain embodiments of the present invention, it may also comprise radiation entering 505 a reference region. The aim of a reference region may be compensating for signal variations not stemming from the interaction with the sample The sensing channel carrying information from the substance may be demultiplexed 506. Certain embodiments of the present invention may also comprise demultiplexing 506 the radiation in the reference channel. Previously discussed techniques (echelle gratings, AWG, ring resonator spectrometers, MZ Fourier transform spectrometers, any other suitable technique) may be used. A plurality of signals is then formed, each signal characterized by a predetermined central wavelength. All the signals may be modulated 507, thus labelling each signal. The modulation can be performed as discussed before (sinusoidal modulation, thermo-optical or electro-optical modulation, etc). The following step may comprise multiplexing 508 the signal in a detector, for example a single pixel photodetector. Multiplexing can be done simultaneously with the modulation or modulation and multiplexing may be performed in separate steps. Because all the multiplexed signals are labelled (for example, modulated with one distinct frequency per signal, the present invention not being limited to this example), the detector provides 509 an output containing all the information of each signal. An additional step comprising 510 demodulation and readout may be performed. For instance, the output may be in the form of a photodetector current (photocurrent) or voltage (photovoltage) as a function of each modulation frequency. Each modulation frequency will have a contribution corresponding to each signal entering the detector. In case a reference channel was used, the sensing signals can be easily compared with each corresponding reference signals. The use of detector arrays can advantageously be avoided. In those applications in which IR radiation is used, for frequencies over 1.6 micrometers (short- and mid-IR frequencies), the heating of the detector system is an important issue as the yield depends on the temperature of the detector system. The use of a single pixel detector instead of a detector array typically may imply a simplification of the cooling circuit and energy savings. Even if the modulation system consumes substantial power (as it would be the case of a thermo-optic modulation system), this power may be compensated by the use of a limited number or a single detector pixel. Due to the different modulation applied to each signal, there is advantageously reduced or avoided cross-talk.

It is an additional advantage of methods according to the present invention that 1/f noise may be reduced thanks to modulation.

The present invention is not limited by any particular embodiment described. A method according to embodiments of the second aspect of the present invention may be implemented using a sensor according to embodiments of the first aspect of the present invention.

Figure 6:
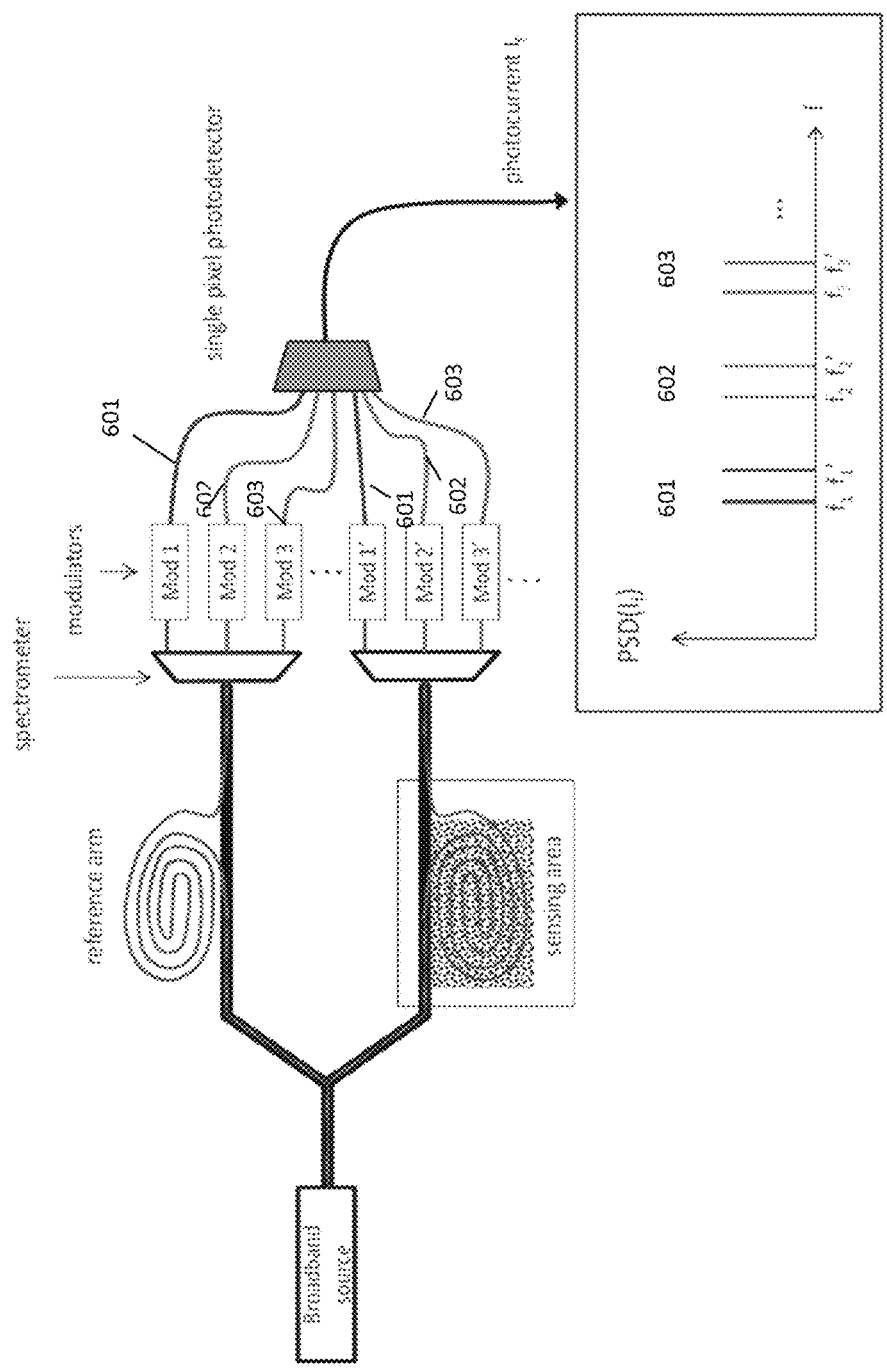
FIG. 6 illustrates a schematic representation of an exemplary system and the resulting output according to an embodiment of the present invention.

By way of example, embodiments of the present invention not being limited thereto, a schematic representation of a system according to an embodiment of the present invention is shown in FIG. 6.

The invention claimed is:

1. An integrated, waveguide based, spectrometer implemented in an integrated photonics circuit, the spectrometer comprising:
   a sensing region configured for receiving multi-wavelength radiation interacting with a sample in the sensing region,
   a wavelength demultiplexing element arranged for capturing said multi-wavelength radiation after interaction with the sample and configured for providing a number of wavelength demultiplexed radiation outputs or a number of different groups of wavelength demultiplexed radiation outputs into different signal carriers, an integrated modulator configured for differently modulating the different demultiplexed radiation outputs or different groups of demultiplexed radiation outputs in the different signal carriers, the integrated modulator being implemented in the integrated photonics circuit, and a multiplexer element configured for multiplexing the differently modulated demultiplexed radiation outputs or the differently grouped demultiplexed radiation outputs.

2. The integrated, waveguide based, spectrometer according to claim 1, wherein the wavelength demultiplexing element and the integrated modulator are an in-plane wavelength demultiplexing element and an in-plane integrated modulator.

3. The integrated, waveguide based, spectrometer according to claim 1, wherein the integrated spectrometer comprises a detector, the detector being a single-pixel detector, and wherein the multiplexer element is configured for multiplexing the outputs towards the detector.

4. The integrated, waveguide based, spectrometer according to claim 1, wherein the spectrometer comprises a reference region, a wavelength demultiplexing element, a modulator and a multiplexer element, for generating corresponding modulated demultiplexed reference output signals or corresponding grouped modulated demultiplexed reference output signals and multiplexing them.

5. The integrated waveguide based spectrometer according to claim 4, wherein modulated demultiplexed reference output signals or grouped modulated demultiplexed reference output signals are directed to a same detector as the differently modulated demultiplexed radiation outputs or the differently grouped demultiplexed radiation outputs stemming from the sensing region.

6. The integrated, waveguide based, spectrometer according to claim 4, wherein the modulator for the reference region and the modulator for the sensing region are configured such that each signal can be unequivocally labeled.

7. The integrated, waveguide based, spectrometer according to claim 1, wherein the system comprises another output coupling element below the detector or wherein the detector is butt-coupled.

8. The integrated, waveguide based, spectrometer according to claim 1, wherein the multiplexer element furthermore comprises a detection functionality for detecting the radiation in the integrated spectrometer as a single pixel detector.

9. The integrated, waveguide based, spectrometer according to claim 1, wherein the multiplexer is a grating array.

10. The integrated, waveguide based, spectrometer according to claim 1, wherein the multiplexer is distanced from the detector and guiding means are provided for directing the multiplexed signal to the detector.

11. The integrated, waveguide based, spectrometer according to claim 1, wherein the modulator is configured for time sequential differently modulating the different demultiplexed radiation outputs or different groups of demultiplexed radiation outputs.

12. The integrated, waveguide based, spectrometer according to claim 1, wherein the modulator is an intensity modulator configured for modulating the different demultiplexed radiation outputs or the different groups of radiation outputs at different frequencies.

13. The integrated, waveguide based, spectrometer according to claim 12, wherein the modulator is adapted for generating orthogonal analog signals of all output channels and/or wherein the modulator is adapted for inducing a sinusoidal modulation of all output channels.

14. The integrated, waveguide based, spectrometer according to claim 1, wherein the modulator is arranged for inducing orthogonal digital coding of the output signals of the different demultiplexed radiation outputs or the different groups of demultiplexed radiation outputs and/or wherein the modulator is arranged for modulating the different demultiplexed radiation outputs or the different groups of demultiplexed radiation outputs, by subsequently shutting all outputs of the demultiplexing element except for one or a group of demultiplexed radiation outputs.

15. The integrated, waveguide based, spectrometer according to claim 1, the spectrometer comprising a detector and the modulator furthermore being adapted for modulating the signals at a frequency outside the 1/f noise of the detector and/or wherein the demultiplexing element comprises any of an echelle grating, an arrayed waveguide grating, a ring resonator based spectrometer, a Combination of Mach-Zehnder interferometer filters, or a Mach-Zehnder Fourier transform spectrometer.

16. The integrated, waveguide based, spectrometer according to claim 1, wherein the modulator is positioned downstream the demultiplexing element with respect to the radiation source providing the multi-wavelength radiation.

17. A method for characterizing a sample property using spectrometry, the method comprising, allowing multi-wavelength radiation in a waveguide structure to interact with a sample to be characterized, demultiplexing the multi-wavelength radiation into different signal carriers after interaction of the multi-wavelength radiation and the sample to be characterized, modulating in an integrated modulator different demultiplexed radiation outputs or different groups of demultiplexed radiation outputs in a different way in the different signal carriers, the integrated modulator being implemented in an integrated photonics circuit, and multiplexing the differently modulated demultiplexed radiation outputs or the differently grouped demultiplexed radiation outputs.

18. The method according to claim 17, wherein said modulating comprises modulating an intensity and/or frequency of the radiation without redirecting the radiation in the modulator and/or wherein the method furthermore comprises splitting multi-wavelength radiation into radiation to be passed through a sensing region, the sensing region being the region where the sample to be characterized is to be positioned, and reference radiation to be passed through a reference region.

19. The method according to claim 18, wherein the method furthermore comprises demultiplexing the multi-wavelength reference radiation passing through the reference region, modulating the different demultiplexed reference radiation outputs or groups of demultiplexed reference radiation outputs in a different way, and multiplexing the differently modulated demultiplexed reference radiation outputs or the differently grouped demultiplexed reference radiation outputs.

20. The method according to claim 19, wherein the reference radiation and the radiation passing through the sensing region are modulated differently for unequivocally labeling the radiation outputs.

* * * * *